United States Patent
Jenneman et al.

(10) Patent No.: US 8,846,732 B2
(45) Date of Patent: Sep. 30, 2014

(54) INHIBITION OF BIOGENIC SULFIDE PRODUCTION VIA BIOCIDE AND METABOLIC INHIBITOR COMBINATION

(75) Inventors: Gary E. Jenneman, Bartsville, OK (US); Anne Greene, Calgary (CA); Gerrit Voordouw, Calgary (CA)

(73) Assignees: ConocoPhillips Company, Houston, TX (US); University Technologies International, Inc., Calgary, Alberta (CA)

( * ) Notice: Subject to any disclaimer, the term of this patent is extended or adjusted under 35 U.S.C. 154(b) by 879 days.

(21) Appl. No.: 12/899,495

(22) Filed: Oct. 6, 2010

(65) Prior Publication Data

US 2011/0020467 A1 Jan. 27, 2011

Related U.S. Application Data

(62) Division of application No. 10/832,116, filed on Apr. 26, 2004, now Pat. No. 7,833,551.

(51) Int. Cl.

| | |
|---|---|
| *A61K 33/00* | (2006.01) |
| *A61K 33/24* | (2006.01) |
| *A61K 31/275* | (2006.01) |
| *A61K 31/4164* | (2006.01) |
| *A61K 31/425* | (2006.01) |
| *A61K 33/42* | (2006.01) |
| *A61K 45/06* | (2006.01) |

(52) U.S. Cl.
CPC .............. *A61K 31/425* (2013.01); *A61K 31/275* (2013.01); *A61K 33/42* (2013.01); *A61K 33/00* (2013.01); *A61K 31/4164* (2013.01); *A61K 45/06* (2013.01)

USPC .............. 514/373; 514/74; 514/693; 514/680; 514/396; 514/521; 514/642; 422/4; 422/6; 422/36; 424/405; 424/718; 424/702

(58) Field of Classification Search
USPC .............. 424/405, 617, 718, 702; 514/373, 74, 514/693, 680, 396, 521, 642; 422/4, 6, 36
See application file for complete search history.

(56) References Cited

U.S. PATENT DOCUMENTS

| | | | |
|---|---|---|---|
| 4,923,899 A | 5/1990 | Wachman et al. | |
| 4,995,987 A | 2/1991 | Whitekettle et al. | |

FOREIGN PATENT DOCUMENTS

| | | |
|---|---|---|
| CA | 2553721 | 11/2005 |
| RU | 1838322 | 8/1993 |
| RU | 2333642 | 3/2008 |
| SU | 1682326 | 10/1991 |

OTHER PUBLICATIONS

Reinsel, "Control of microbial souring by nitrate, nitrite or glutaraldehyde injection in a sandstone column", Journal of Industrial Microbiology, Aug. 1996, vol. 17, Issue 2, pp. 128-136.*

* cited by examiner

*Primary Examiner* — Sreeni Padmanabhan
*Assistant Examiner* — Sahar Javanmard
(74) *Attorney, Agent, or Firm* — Boulware & Valoir

(57) ABSTRACT

Biogenic sulfide production is synergistically inhibited by treating sulfate-reducing bacteria (SRB) with a biocide and a metabolic inhibitor. The biocide directly kills a first portion of the SRB. The metabolic inhibitor inhibits sulfate-reducing growth of a second portion of the SRB without directly killing the second portion of the SRB. The treatment of SRB with both a biocide and a metabolic inhibitor provides effective biogenic sulfide inhibition at significantly lower concentrations than would be required if the biocide or metabolic inhibitor was used alone.

19 Claims, No Drawings

US 8,846,732 B2

INHIBITION OF BIOGENIC SULFIDE PRODUCTION VIA BIOCIDE AND METABOLIC INHIBITOR COMBINATION

CROSS-REFERENCE TO RELATED APPLICATIONS

This application is a divisional application of U.S. application Ser. No. 10/832,116 filed Apr. 16, 2004, which is hereby incorporated by reference in its entirety.

BACKGROUND OF THE INVENTION

1. Field of the Invention

The present invention relates generally to the control of biogenic sulfide production. In another aspect, the invention concerns the use of at least one biocide and at least one metabolic inhibitor to synergistically inhibit sulfide production by sulfate-reducing bacteria.

2. Description of the Prior Art

The presence of sulfides (e.g., $H_2S$, $HS^-$, and $S^{2-}$) in fluids poses serious problems due to their toxicity, odor, and corrosive nature. It is well known that the presence of sulfides in many fluids is a consequence of the reduction of sulfates to sulfides by sulfate-reducing bacteria (SRB). SRB are routinely found in water associated with oil production systems and can be found in virtually all industrial aqueous processes including, for example, cooling-water systems, pulp and paper-making systems, chemical manufacturing, and petroleum refining.

Requirements for SRB activity and growth include a substantially anaerobic aqueous environment containing adequate nutrients, an electron donor, and an electron acceptor. A typical electron acceptor is sulfate, which produces $H_2S$ upon reduction. A typical electron donor is a volatile fatty acid (e.g., acetic or propionic acids), although hydrogen can also function as an electron donor. Conditions in an oil reservoir subjected to seawater flooding are excellent for establishing SRB activity. Seawater contains a significant concentration of sulfate, while connate, or indigenous formation, water contains volatile fatty acids and other required trace nutrients (e.g., nitrogen and phosphorus). Conditions within industrial water systems, such as effluent streams from production operations or cooling water streams, are also conducive to SRB activity due to the anaerobic biofilm which is formed on pipeline, tank, or vessel walls. The same is true within the sewers and other piping and facilities associated with municipal wastewater handling systems.

Hydrogen sulfide ($H_2S$) is corrosive and reacts with metal surfaces to form insoluble iron sulfide corrosion products. In oilfield operations, $H_2S$ partitions into the water, oil, and natural gas phases of produced fluids and creates a number of problems. For instance, oil and gas that contain high levels of $H_2S$ have a lower commercial value than low-sulfide oil and gas. Removing biogenic $H_2S$ from sour oil and gas increases the cost of these products. In addition, $H_2S$ is an extremely toxic gas and can be lethal to humans at even small concentrations. Its presence in wastewater systems poses a threat to worker safety. The discharge of produced waters containing high levels of $H_2S$ into aquatic or marine environments is hazardous because $H_2S$ reacts with oxygen and lowers the dissolved-oxygen levels in the water.

Corrosion caused by SRB-produced $H_2S$ frequently results in extensive damage. Pipe systems, tank bottoms, and other pieces of equipment can rapidly fail if they have areas where microbial corrosion occurs. If a failure occurs in a pipeline or storage tank bottom, the released fluid can have serious environmental consequences. If a failure occurs in a high pressure water or gas line, the consequences may be worker injury or death. Any such failure involves substantial repair or replacement costs.

In the past there have been two main approaches to reducing the level of sulfides in industrial fluids. One approach involved removing sulfides from the fluids after their formation. This post-formation removal approach, however, was frequently uneconomical or impractical, especially in oilfield operations. The other approach has been to treat the SRB-containing fluids with biocides or metabolic inhibitors to thereby kill or inhibit the growth of the SRB prior to significant biogenic sulfide formation. However, in many instances high concentrations of biocides or metabolic inhibitors are required to effectively inhibit sulfide production by SRB. The costs associated with employing biocides or metabolic inhibitors in such high concentrations can be prohibitive.

OBJECTS AND SUMMARY OF THE INVENTION

It is, therefore, an object of the present invention to provide a method and composition for more effectively and economically inhibiting biogenic sulfide production.

Another object of the present invention is to provide a composition that is effective to inhibit sulfide production by SRB at relatively low concentrations of the inventive composition.

It should be understood that the above-listed objects are only exemplary. Further objects and advantages of the present invention will be apparent from the detailed description of the preferred embodiment, the claims, and the drawing figures.

Accordingly, one aspect of the present invention concerns a method of inhibiting sulfide production by SRB. The method comprises the steps of: (a) contacting the SRB with a first concentration of a biocide component, wherein the first concentration is less than about 90% of the minimum inhibitory concentration (MIC) of the biocide component; and (b) contacting the SRB with a second concentration of a metabolic inhibitor component, wherein the second concentration is less than about 90% of the MIC of the metabolic inhibitor component.

Another aspect of the present invention concerns a method comprising contacting SRB with a treated medium comprising an aldehyde and a metabolic inhibitor. The metabolic inhibitor is selected from the group consisting of nitrite, molybdate, and combinations thereof. The aldehyde and the metabolic inhibitor are present in the treated medium in an aldehyde to metabolic inhibitor molar ratio in the range of from about 50:1 to about 1:50.

Still another aspect of the present invention concerns a composition for effectively inhibiting sulfide production by SRB. The composition comprises: (a) a biocide component capable of directly killing a first portion of the SRB; and (b) a metabolic inhibitor component capable of inhibiting the sulfate-reducing growth of a second portion of the SRB without directly killing the second portion of the SRB. The biocide component is present in the composition in a first concentration that is less than about 90% of the MIC of the biocide component. The metabolic inhibitor component is present in the composition in a first concentration that is less than about 90% of the MIC of the biocide component.

A further aspect of the present invention concerns a composition comprising an aldehyde and a metabolic inhibitor selected from the group consisting of nitrite, molybdate, and combinations thereof. The aldehyde and the metabolic inhibitor are present in the composition in an aldehyde to metabolic inhibitor molar ratio in the range of from about 50:1 to about 1:50.

DETAILED DESCRIPTION OF THE PREFERRED EMBODIMENT

We have discovered that sulfide production by sulfate-reducing bacteria (SRB) can be more effectively and economically inhibited by treating the SRB with certain synergistic combinations of biogenic sulfide inhibitors (BSIs). As used herein, "sulfate-reducing bacteria" or "SRB" shall denote one or more types of bacterium capable of facilitating the reduction of sulfates to sulfides. As used herein, "biogenic sulfide inhibitor" or "BSI" shall be used as a generic term to denote any compound that effectively inhibits sulfide production by at least one type of sulfate-reducing bacterium. BSIs of particular significance in the present invention include biocides and metabolic inhibitors. As used herein, "biocide" shall denote a compound that directly kills at least one type of sulfate-reducing bacterium via contact therewith. As used herein, "metabolic inhibitor" shall denote a compound that effectively inhibits the sulfate-reducing activity of at least one type of sulfate-reducing bacterium, without directly killing the inhibited sulfate-reducing bacterium upon contact therewith. Metabolic inhibitors deprive SRB of the ability to produce ATP and, as a result, cells are unable to grow and/or divide. This inability to grow or divide may eventually cause the death of some of the SRB; however, the cell death is not a direct result of exposure to the metabolic inhibitors as it would be for biocides.

In accordance with one embodiment of the present invention, SRB are contacted with a treated medium comprising more than one BSI to thereby synergistically inhibit biogenic sulfide production. Preferably, the treated medium comprises at least one biocide and at least one metabolic inhibitor. Biocides suitable for use in the present invention include both oxidizing and non-oxidizing biocides. Preferably, non-oxidizing biocides are employed. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., bronopol and 2-2-dibromo-3-nitrilopropionamide (DBNPA)), sulfur compounds (e.g., isothiazolone, carbamates, and metronidazole), and quaternary phosphonium salts (e.g., tetrakis (hydroxymethyl) phosphonium sulfate (THPS)). Metabolic inhibitors suitable for use in the present invention include, for example, nitrite, molybdate, tungstate, selenate, and anthraquinone. Other equivalent metabolic inhibitors for SRB may exist, but are not known or foreseeable at the time of filing of this patent.

The synergistic inhibitory effect resulting from the combined use of more than one BSI (e.g., a biocide and a metabolic inhibitor) can be demonstrated by comparing the inhibitory effect of the combined BSIs with the inhibitory effect of each individual BSI, when used alone. This synergistic inhibitory effect can be quantified by comparing the concentrations of the combined BSIs necessary to provide effective biogenic sulfide inhibition with the concentrations of each individual BSI necessary to provide effective sulfide inhibition when each individual BSI is used alone.

The concentration of an individual BSI necessary to effectively inhibit sulfide production by SRB can be expressed as a minimum inhibitory concentration (MIC). As used herein, "minimum inhibitory concentration" or "MIC" shall denote the minimum concentration of an individual BSI necessary to prevent sulfide production by SRB for 30 days after contact with the SRB is initiated. Each BSI has a unique MIC. For example, we have found that under certain test conditions, a 5 mM (milliMolar) concentration of glutaraldehyde (biocide) in a certain treated medium is the minimum concentration of glutaraldehyde necessary to prevent sulfide production by certain SRB for 30 days after the treated medium is first contacted with the SRB. Thus, under the conditions of this test, the MIC of glutaraldehyde is 5 mM.

This patent uses the MIC of various BSIs as a reference to demonstrate that synergistic biogenic sulfide inhibition can be achieved when certain combinations of BSIs are employed at concentrations that are substantially less than the MIC of each individual BSI. Thus, the amount or concentration of a particular BSI used to treat the SRB can be expressed as a percentage of the MIC of that particular BSI. It should be noted, however, that the MIC of a particular BSI can vary, depending upon numerous factors such as, for example, the type of SRB treated, the composition of the treated medium, and the temperature at which the SRB and treated medium are maintained. Thus, when SRB are treated with an amount of a particular BSI that is expressed as a percentage of the MIC for that BSI, it is assumed that the MIC for that BSI was determined at the same conditions under which the SRB are currently being treated. For example, if a certain treated medium comprising glutaraldehyde and nitrite is used to treat certain SRB under certain conditions and the treated medium contains glutaraldehyde at 50% (by mole) of the MIC of glutaraldehyde, then the concentration of glutaraldehyde in the treated medium is one-half the concentration of glutaraldehyde alone (i.e., without nitrite) in the treated medium that would be necessary to prevent sulfide production by the SRB for 30 days under the same conditions.

One embodiment of the present invention can be carried out by contacting SRB with at least one biocide and at least one metabolic inhibitor in either a simultaneous or sequential fashion. Preferably, the biocide and metabolic inhibitor components are simultaneously contacted with the SRB by first combining the biocide (and/or a precursor of the biocide) and metabolic inhibitor (and/or a precursor of the metabolic inhibitor) in a treated medium and contacting the SRB with the treated medium. Nitrate is one example of a precursor of nitrite. The specific composition of the treated medium can vary greatly, depending upon the particular application for which biogenic sulfide inhibition is sought. Thus, the treated medium can be any medium suitable for carrying the biocide and metabolic inhibitor components. Preferably, the treated medium is an aqueous-based medium, more preferably the treated medium comprises at least about 2% water by weight, more preferably at least about 50% water by weight, and most preferably at least 90% water by weight. The SRB with which the treated medium is contacted can reside in the treated medium itself or on a surface (e.g., the surface of a subterranean formation or the inner surface of a pipe or vessel) with which the treated medium comes into contact. In one application, the treated medium is brine (e.g., oilfield brine) that contains sulfates, SRB, a biocide, and a metabolic inhibitor. In certain instances, the biocide may be present as part of conventional oilfield chemicals, such as corrosion inhibitors. Thus, it may be preferred to employ biocides that exhibit other advantageous properties such as corrosion inhibition. For example, quaternary amines are good biocides and corrosion inhibitors.

The synergistic inhibition provided by the combined biocide and metabolic inhibitor components of the treated medium allow for effective biogenic sulfide inhibition at concentrations substantially less than the minimum inhibitory concentrations (MICs) of the individual components. Thus, it is preferred for the concentrations of the biocide and the metabolic inhibitor components of the treated medium to be less than the MICs of the individual biocide and metabolic inhibitor components. More preferably, the concentrations of both the biocide and the metabolic inhibitor are less than about 90% of their respective MICs. Still more preferably, the concentrations of one or both the biocide and the metabolic inhibitor are less than about 75% of their respective MICs. Even more preferably, the concentrations of one or both of the biocide and the metabolic inhibitor are less than about 50% of their respective MICs. Yet still more preferably, the concentrations of one or both the biocide and the metabolic inhibitor are less than about 35% of their respective MICs. Most preferably, the concentrations of one or both the biocide and the metabolic inhibitor are less than 25% of their respective MICs.

In a preferred embodiment of the present invention, the biocide is an aldehyde and the metabolic inhibitor is nitrite and/or molybdate. When the biocide is an aldehyde and the metabolic inhibitor is nitrite and/or molybdate it is preferred for the treated medium to have a biocide to metabolic inhibitor molar ratio in the range of from about 50:1 to about 1:50, more preferably about 20:1 to about 1:20, still more preferably about 10:1 to about 1:10, and most preferably 5:1 to 1:5. In addition, when the biocide is an aldehyde, it is preferred for the concentration of the biocide in the treated medium to be in the range of from about 0.1 to about 5 mM, (milliMolar) more preferably about 0.1 to about 3 mM, and most preferably 0.1 to 2 mM. When the metabolic inhibitor is nitrite and/or molybdate, it is preferred for the concentration of the metabolic inhibitor in the treated medium to be in the range of from about 0.1 to about 5 mM, more preferably about 0.1 to about 3 mM, and most preferably 0.1 to 2 mM. In a particularly preferred embodiment of the present invention, the biocide component contacted with the SRB consists essentially of glutaraldehyde and the metabolic inhibitor component contacted with the SRB consists essentially of nitrite.

The treated medium and the SRB can be contacted in either an intermittent (i.e., batch) or continuous fashion. Preferably, the present invention is carried out in a substantially continuous manner. In either case, the concentrations of the biocide and metabolic inhibitor components, described above, are expressed as time-averaged concentrations. For example, if SRB is contacted with a treated medium in a batch mode having a frequency of once every 24 hours (1440 minutes), a duration of 14.4 minutes, and a batch concentration of 100 mM, the average concentration would be 1 mM (i.e., 100 mM×14.4 min/1440 min). The following example is intended to be illustrative of the present invention and to teach one of ordinary skill in the art to make and use the invention. This example is not intended to limit the invention in any way.

EXAMPLE

In this Example, the effect of various biocide and metabolic inhibitor combinations and concentrations were investigated to determine their combined effect on sulfide production by SRB.

The sulfate-reducing bacterial (SRB) consortium used in this study was enriched from produced water obtained from the Coleville oil field near Kindersely, Sadkatchewan, Canada. Serial enrichment in saline Postgate C medium (sPGC) resulted in a stable SRB consortium that was maintained for over one year prior to commencement of the biocide and metabolic inhibitor exposure experiments, described below. The SRB consortium was maintained by weekly transfer in sPGC medium, and incubated at 30° C. Saline Postgate C medium (sPGC) is a modification of medium C described in Postgate, J. R. *The Sulfate-Reducing Bacteria*. Cambridge: Cambridge University Press, pp. 30-34 (1984). The sPGC contained the following components per 1 liter of distilled water: 7 g NaCl; 1.2 g $MgCl_2$ $6H_2O$; 0.5 g $KH_2PO_4$; 1 g $NH_4Cl$; 4.5 g $Na_2SO_4$; 0.042 g $CaCl_2$ $2H_2O$; 0.03 g $MgSO_4$ $7_2O$; 0.004 g $FeSO_47H_2O$; 0.28 g sodium citrate; 10 g 60% sodium lactate; 1 g yeast extract; and a trace amount of rezazurin.

The cultures used in this study were grown in 100 mL of modified Coleville synthetic brine medium (mCSB) in 160-ml serum bottles, with a headspace of 5% $H_2$, 10% $CO_2$ balance $N_2$. The mCSB is described in Nemati M., Jenneman G. E., Voordouw G. *A mechanistic study on microbial control of souring in oil reservoirs*. Biotechnol. Bioeng. 74:424-434 (2001). The mCSB contained the following components per 950 milliliters of distilled water: 7 g NaCl; 0.027 g $KH_2PO_4$; 0.02 g $NH_4Cl$; 0.24 g $CaCl_2$ $2H_2O$; 0.68 g $MgSO_4$ $7H_2O$; 1 g $(NH_4)_2SO_4$; 0.68 g sodium acetate; 5.6 g sodium lactate syrup (60% v/v); 1.9 g $NaHCO_3$; and 50 ml micronutrient solution. The micronutrient solution contained the following components per 990 ml of distilled water: 2 g nitrilotriacetic acid; 0.006 g $FeCl_3$; 1.2 g $CaSO_4$ $2H_2O$; 2 g $MgSO_4$ $7H_2O$; 0.16 g NaCl; 1.4 g $Na_2HPO_4$; 0.72 $KH_2PO_4$; and 10 ml trace element solution. The 10 ml trace element solution contained the following components: 0.5 ml $H_2SO_4$; 2.28 g $MnSO_4$ $H_2O$; 0.5 g $ZnSO_4$ $7H_2O$; 0.5 g $H_3BO_3$ 0.025 g $CuSO_4$ $5H_2O$; 0.025 g $NaMoO_4$ $2H_2O$; and 0.045 g $CoCl_2$ $6H_2O$.

A 2% inoculum of freshly grown Coleville SRB enrichment was used in all cases. After inoculation, cultures were incubated overnight at 30° C., until the produced sulfide in the cultures was approximately 5 milliMolar (mM) (maximum concentration of produced sulfide in these cultures is approximately 12 mM). At this time, the biocide/metabolic inhibitor combinations were added. Cultures were incubated for 1 month after the addition of the biocide and metabolic inhibitor. If sulfate reduction and sulfide production resumed during the 1-month incubation period, inhibition was deemed unsuccessful.

Sulfate was measured using the turbidimetric method described in: American Public Health Association, *Standard Methods for the Examination of Water and Wastewater*. Washington, D.C.: American Water Works Association and Water Pollution Control Federation, pp. 439-440 (1992) as modified by the method described in Nemati M., Jenneman G. E., Voordouw G., *A mechanistic study on microbial control of souring in oil reservoirs*, Biotechnol. Bioeng. 74:424-434 (2001). Sulfide was analyzed by the colorimetric method described in Cord-Ruwisch, R., *A quick method for determination of dissolved and precipitated sulfides in cultures of sulfate-reducing bacteria*, J. Microbiol. Meth. 4:33-36 (1985). Nitrite was evaluated by the colorimetric method described in Nemati M., Jenneman G. E., Voordouw G., *A mechanistic study on microbial control of souring in oil reservoirs*, Biotechnol. Bioeng. 74:424-434 (2001). Cell growth was not monitored; the optical density and color of various cultures changed significantly upon addition of some biocides or inhibitors, which interfered with optical density readings.

Various combinations of biocides and metabolic inhibitors were tested. For the purpose of this example, biocides are defined as agents that kill microorganisms directly. The two metabolic inhibitors tested are both specific to SRB and are known to interfere with different stages of sulfate reduction to sulfide. Inhibition of sulfate reduction deprives SRB of the ability to produce ATP (the cellular energy currency), thus cells are unable to grow or divide and may eventually die, however cell death is not necessarily a result of exposure to these compounds, particularly at low concentrations where energy production might be decreased but not completely inhibited.

For each biocide and metabolic inhibitor tested, the minimum inhibitory concentration (MIC; the minimum amount of biocide required to inhibit sulfate reduction and sulfide production in the SRB culture for one month) was determined. Combinations of pairs of biocides were tested at various concentrations to determine the MICs of several concentrations of each when mixed. The effectiveness of various biocide combinations was evaluated. Biocide combination effects were separated into five categories: antagonistic (one biocide had a negative effect on another such that more than the MIC for one biocide alone plus the second biocide at any amount was required for inhibition), additive (e.g., inhibition requires 25% of the MIC of one biocide and 75% of the other, or vice versa), indifferent, less than additive (more than an additive amount of the pair of biocides, but less than the MIC of each, is required for inhibition) or synergistic (less than an additive amount of the pair of biocides is required for inhibition).

The metabolic inhibitors evaluated were molybdate and nitrite. Six nonoxidizing biocides were evaluated alone and in combination with nitrite or molybdate (oxidizing biocides were not considered in this study). Both glutaraldehyde and formaldehyde are aldehyde-type biocides. Benzalkonium chloride is a representative of the quaternary amine group of biocides. Combinations of quaternary amine biocides and glutaraldehyde are commercially available for use in oilfield and other situations. Cocodiamines are from the amine and diamine biocide group. The cocodiamine biocide used in this study was T-397, provided by Brenntag Canada. Bronopol (2-brono-2-nitropropane-1,3-diol) is a halogenated biocide. Tetrakis(hydroxymethyl)phosphonium sulfate (THPS) is a quaternary phosphonium salt. Biocides from several groups commonly used in oil field situations were purposely chosen in order to allow a general evaluation of the effectiveness of each group when combined with specific metabolic inhibitors.

The test results for combinations of various biocides with the metabolic inhibitors (nitrite or molybdate) are discussed below. Combinations of several biocides with nitrite or molybdate resulted in synergistic inhibitory effects. In particular, nitrite plus glutaraldehyde or benzalkonium chloride and molybdate plus glutaraldehyde showed a strong synergistic effect. Nitrite plus Bronopol produced a lesser synergistic effect. Nitrite plus cocodiamine and molybdate plus benzalkonium chloride, cocodiamine, or Bronopol produced the smallest synergistic effect. Nitrite plus THPS and molybdate plus THPS showed a less than additive effect. This less than additive effect with THPS could be an isolated phenomenon for the particular SRB and conditions employed in this study. No combinations tested produced indifferent or antagonistic effects. Thus, all combinations other than those with THPS resulted in better than additive inhibitory effects.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A composition for effectively inhibiting sulfide production by sulfate-reducing bacteria (SRB), said composition comprising a synergistic combination of:
   (a) a non-oxidizing biocide component capable of directly killing a first portion of the SRB, wherein said biocide component is present in the composition in a first concentration that is less than about 50% of the minimum inhibitory concentration (MIC) of the biocide component, wherein said biocide component is selected from the group consisting of formaldehyde, glutaraldehyde, acrolein, cocodiamine, bronopol, 2-2-dibromo-3-nitrilo-propionamide (DBNPA), isothiazolone, metronidazole, and combinations of one or more thereof; and
   (b) a metabolic inhibitor component capable of inhibiting the sulfate-reducing growth of a second portion of the SRB without directly killing the second portion of the SRB, wherein said metabolic inhibitor component is present in the composition in a first concentration that is less than about 50% of the MIC of the biocide component, wherein said metabolic inhibitor component is selected from the group consisting of nitrite, molybdate, tungstate, selenate, anthraquinone, and combinations of one or more thereof.

2. The composition of claim 1, wherein at least one of said first and second concentrations is less than about 35% of its MIC.

3. The composition of claim 1, wherein said at least one of first and second concentrations is less than 25% of its MIC.

4. The composition of claim 3, wherein said first and second concentrations are both less than about 35% of their respective MICs.

5. The composition of claim 1, wherein said biocide component is a combination of more than one individual biocide and/or said metabolic inhibitor component is a combination of more than one individual metabolic inhibitor.

6. The composition of claim 1, wherein said biocide component comprises substantially no tetrakis hydroxymethyl phosphonium sulfate (THPS).

7. The composition of claim 1, wherein said biocide component comprises glutaraldehyde and said metabolic inhibitor component comprises nitrite.

8. The composition of claim 1, wherein said biocide component consists essentially of glutaraldehyde and said metabolic inhibitor component consists essentially of nitrite.

9. The composition of claim 1, further comprising at least about 2% by weight water.

10. The composition of claim 1, further comprising at least 50% by weight water.

11. A synergistic composition comprising: (a) an biocide aldehyde, selected from the group consisting of formaldehyde, glutaraldehyde, and combinations thereof; and (b) a metabolic inhibitor selected from the group consisting of nitrite, molybdate, and combinations thereof, wherein said aldehyde and said metabolic inhibitor are each present in the composition at ≤50% MIC and in an aldehyde to metabolic inhibitor molar ratio in the range of from about 50:1 to about 1:50.

12. The composition of claim 11, wherein said metabolic inhibitor comprises nitrite.

13. The composition of claim 11, wherein said aldehyde biocide comprises glutaraldehyde.

14. The composition of claim 11, wherein said aldehyde to metabolic inhibitor molar ratio is in the range of from about 20:1 to about 1:20.

15. The composition of claim 11, wherein said aldehyde to metabolic inhibitor molar ratio is in the range of from 10:1 to 1:10, wherein said metabolic inhibitor consists essentially of nitrite, and wherein said biocide consists essentially of glutaraldehyde.

16. The composition of claim 11, wherein said aldehyde and said metabolic inhibitor are each present in the composition in a concentration in the range of from about 0.1 mM to about 5 mM.

17. The composition of claim 11, wherein said aldehyde and said metabolic inhibitor are each present in the composition in a concentration in the range of from about 0.1 mM to about 2 mM.

18. The composition of claim 11, wherein said aldehyde comprises glutaraldehyde and said metabolic inhibitor comprises nitrite.

19. The composition of claim 11, wherein said aldehyde consists essentially of glutaraldehyde and said metabolic inhibitor consists essentially of nitrite.

* * * * *